United States Patent [19]
Knittel et al.

[11] Patent Number: 5,885,823
[45] Date of Patent: *Mar. 23, 1999

[54] *LAWSONIA INTRACELLULARIS* CULTIVATION, ANTI-*LAWSONIA INTRACELLULARIS* VACCINES AND DIAGNOSTIC AGENTS

[75] Inventors: Jeffrey P. Knittel; Michael B. Roof, both of Ames, Iowa

[73] Assignee: NOBL Laboratories, Inc., Sioux Center, Iowa

[*] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,714,375.

[21] Appl. No.: 658,194

[22] Filed: Jun. 4, 1996

Related U.S. Application Data

[63] Continuation-in-part of Ser. No. 465,337, Jun. 5, 1995, Pat. No. 5,714,375.

[51] Int. Cl.$^6$ ............................... C12N 1/20; C12N 1/00; A61K 39/02
[52] U.S. Cl. ...................... 435/243; 435/245; 435/252.1; 435/366; 435/383; 435/395; 435/403; 424/93.4; 424/234.1; 424/825
[58] Field of Search ............................... 424/234.1, 93.4, 424/825; 435/245, 252.1, 366, 383, 395, 403, 243

[56] References Cited

U.S. PATENT DOCUMENTS

| | | |
|---|---|---|
| 4,132,597 | 1/1979 | Kvanta . |
| 4,237,218 | 12/1980 | Monthony et al. . |
| 4,880,739 | 11/1989 | Yamada et al. . |
| 4,904,597 | 2/1990 | Inoue et al. . |
| 4,920,048 | 4/1990 | Diderichsen . |
| 5,126,265 | 6/1992 | Cidaria et al. . |
| 5,230,912 | 7/1993 | Yajima et al. . |
| 5,296,221 | 3/1994 | Mitsuoka et al. . |
| 5,318,908 | 6/1994 | Seki et al. . |
| 5,338,670 | 8/1994 | Sekura et al. . |
| 5,380,657 | 1/1995 | Schaefer et al. . |
| 5,436,001 | 7/1995 | Krawer . |
| 5,610,059 | 3/1997 | Joens et al. . |

OTHER PUBLICATIONS

Brock, Thomas D. et al., "Immunization for Infectious Disease", Biology of Microorganisms, Prentice–Hall, Inc., 4th Ed., (19 ), pp. 557–558.
McOrist et al., Porcine Proliferative Enteropathy, *The Veterinary Record* vol. 132, p. 368, 1993.
Lawson et al., Attempts to Cultivate the Campylobacter–like Organism of the Proliferative Enteropathies, *Assoc. of Vet. Teachers and Research Workers*, Abstract, Apr. 8–11, 1990.
S. Jasni et al., "Reproduction of Proliferative Enteritis in Hamsters With a Pure Culture of Porcine Ileal Symbiont Intracellularis", *Veterinary Microbiology* 41, pp. 1–9 (1994).
S. McOrist et al., "Synergism of Ileal Symbiont Intracellularis and Gut Bacteria in The Reproduction of Porcine Proliferative Enteropathy", *Veterinary Record*, 134, pp. 331–332 (1994).
S. McOrist et al., "Antimicrobial Susceptibility of Ileal Symbiont Intracellularis Isolated From Pigs With Proliferative Enteropathy", *Journal of Clinical Microbiology*, 33, pp. 1314–1317 (1995).
S. McOrist et al., "Entry of the Bacterium Ileal Symbiont Interacellularis Into Cultured Enterocytes and its Subsequent Release", *Research in Veterinary Science*, 59, pp. 255–260 (1995).
S. McOrist, et al., In Vitro Testing Of Antimicrobial Agents For Proliferative Enteropathy (Ileitis), *Swine Health and Production*, pp. 146–149 (Jul. and Aug. 1995).
S. McOrist et al., "Characterization of *Lawsonia intracellularis* gen. nov., sp. nov., the Obligately Intracellular Bacterium of Porcine Proliferative Enteropathy", *International Journal of Systematic Bacteriology*, 45, pp. 820–825 (1995).
G.H.K. Lawson et al., "Infection of Cultured Rat Enterocytes by Ileal Symbiont Intracellularis Depends on Host Cell Function and Actin Polymerisation", *Veterinary Microbiology*, 45, pp. 339–350 (1995).
S. McOrist et al., Vet. Pathol., vol. 26, 260–67 (1989).
S. McOrist et al., Vet. Pathol., vol. 26, 260–64 (1989).
C. Gebhart et al., Int'l J. of Systemic Bacteriology, vol. 43, No. 3, 533–38 (1993).
S. McOrist et al., Infection and Immunity, vol. 61, No. 10, 4286–92 (1993).
G. Lawson et al., J. of Clinical Microbiology, vol. 31, No. 5, 1136–42 (1993).
H. Stills, Infection and Immunity, vol. 59, No. 9, 3227–36 (1991).
S. McOrist et al., Int'l. J. of Systemic Bacteriology, vol. 45, No. 4, 820–25 (1995).
S. McOrist et al., Vet. Rec. 121:421–422 (1987).
Jones et al., J. Clin. Microbiol., 31:2611–2615 (1993).
McOrist et al., Vet. Microbiaol. 41 (1994) 205–212.
Gary F. Jones as reported in his Ph.D. thesis, University of Minnesota, Minneapolis, MN (Jun. 1993).
Peace et al., Comparative Analysis of the 16S rRNA Gene Sequence of the Putative Agent of Proliferative Ileitis of Hamsters, *Int'l. J. of Syst. Bacter.* vol. 44, pp. 832–835, 1994.
Tseneva et al., Invasiveness and Cytotoxicity as Criteria Used for the Evaluation of the Attenuation of Yersinia, *Zh Mikrobiol. Epidemiol. Immunobiol.* 1988 (Biosis Abstract No. 89:224753).

*Primary Examiner*—Paula K. Hutzell
*Assistant Examiner*—Khalid Masood
*Attorney, Agent, or Firm*—Dickstein Shapiro Morin & Oshinsky LLP

[57] ABSTRACT

A method for large scale cultivation and attenuation of *L. intracellularis* bacteria by inoculating cells with *L. intracellularis* bacteria to infect the cells, incubating the infected cells in a reduced oxygen concentration and maintaining the infected cells in suspension. Anti-*L. intracellularis* vaccines are prepared from cultures grown in suspension. Diagnostic agents are also disclosed.

17 Claims, No Drawings

LAWSONIA INTRACELLULARIS CULTIVATION, ANTI-LAWSONIA INTRACELLULARIS VACCINES AND DIAGNOSTIC AGENTS

This application is a continuation-in-part of U.S. patent application Ser. No. 08/465,337 (U.S. Pat. No. 5,714,375) filed Jun. 5, 1995.

FIELD OF THE INVENTION

The present invention is directed to anti-*Lawsonia intracellularis* vaccines and methods for protecting against and diagnosing *Lawsonia intracellurlaris* infection. The products and processes of the invention are attainable, in part, as the result of the improved method which we have discovered for cultivating large scale supplies of *L. intracellularis*.

DESCRIPTION OF THE RELATED ART

*L. intracellularis*, the causative agent of porcine proliferative enteropathy ("PPE"), affects virtually all animals, including humans, rabbits, ferrets, hamsters, fox, horses, and other animals as diverse as ostriches and emus.

*L. intracellularis* is a particularly great cause of losses in swine herds. Estimates of the prevalence and incidence of PPE in the U.S. have been as high as 20 percent of the swine herd with estimated losses of $20 million annually.

A consistent feature of PPE is the occurrence of intracytoplasmic, non-membrane bound curved bacilli within enterocytes in affected portions of intestine. The bacteria associated with PPE have been referred to as "Campylobacter-like organisms." S. McOrist et al., Vet. Pathol., Vol. 26, 260–64 (1989). Subsequently, the causative bacteria have been identified as a novel taxonomic genus and species, vernacularly referred to as *Ileal symbiont* (IS) intracellularis. C. Gebhart et al., Int'l. J. of Systemic Bacteriology, Vol. 43, No. 3, 533–38 (1993). More recently, these novel bacteria have been given the taxonomic name *Lawsonia (L.) intracellularis*. S. McOrist et al., Int'l. J. of Systemic Bacteriology, Vol. 45, No. 4, 820–25 (1995). These three names have been used interchangeably to refer to the same organism as further identified and described herein. We have endeavored to use the taxonomic name, *L. intracellularis*, throughout the discussion of the present invention.

*L. intracellularis* is an obligate, intracellular bacterium which cannot be cultured by normal bacteriological methods on conventional cell-free media and has been thought to require attached epithelial cells for growth. S. McOrist et al., Infection and Immunity, Vol. 61, No. 10, 4286–92 (1993) and G. Lawson et al., J. of Clinical Microbiology, Vol. 31, No. 5, 1136–42 (1993) discuss cultivation of *L. intracellularis* using IEC-18 rat intestinal epithelial cell monolayers in conventional tissue culture flasks. In addition, H. Stills, Infection and Immunity, Vol. 59, No. 9, 3227–36 (1991) discusses using Intestine 407 human embryonic intestinal cell monolayers and GPC-16 guinea pig colonic adenocarcinoma cell monolayers in conventional tissue culture flasks. These prior cultivation methods are labor intensive and are not suitable for scale-up.

The current understanding of *L. intracellularis* infection and the treatment and effective control of the disease have been seriously hampered by the fastidious growth requirements of *L. intracellularis* in in vitro cultures. There is currently a need for an improved method for cultivation of *L. intracellularis*. There is also a need for anti-*L. intracellularis* vaccines and effective tools for diagnosing *L. intracellularis* infection.

SUMMARY OF THE INVENTION

One object of the invention is to provide anti-*L. intracellularis* vaccines.

Another object of the invention is to provide methods for detecting the presence of antibodies to *L. intracellularis* in biological samples.

A further object is to provide an improved cultivation method allowing large scale cultivation of *L. intracellularis* for production of vaccines and diagnostic agents.

To achieve these and other objects, and in accordance with the purpose of the invention as embodied and broadly described herein, the present invention provides a method for cultivating *L. intracellularis* and large scale supplies of bacteria produced thereby. According to the method, *L. intracellularis* bacteria are incubated in an oxygen concentration of from about 0 percent to about 18 percent, while agitating the bacteria to cultivate the *L. intracellularis* while maintaining the bacteria in suspension.

According to another embodiment, a method is provided for cultivating *L. intracellularis* bacteria by inoculating an HEp-2, McCoys, or IEC-18 cell monolayer, which is at about 30 percent confluency, with an inoculum comprising *L. intracellularis* bacteria so as to infect the cells with the bacteria. The infected cells are then incubated at a temperature of about 36 to about 38° C. at an oxygen concentration of about 0 percent to about 8.0 percent until the cells reach confluency. The infected cells and growth media are then placed in a fermentor, bioreactor, spinner flask or other container suitable for maintaining the cells in suspension. The infected cells are incubated while agitating the cells so as to cultivate the *L. intracellularis* bacteria while maintaining the infected cells in suspension. A portion of the cultivated *L. intracellularis* is then passaged to fresh culture cells to increase the production of *L. intracellularis* bacteria.

The invention provides anti-*L. intracellularis* vaccines and methods for producing vaccines against *L. intracellularis*. An avirulent *L. intracellularis* bacteria is produced by passaging the cultivated *L. intracellularis* bacteria a sufficient number of times and selecting for an attenuated strain, or by subjecting the cultivated bacteria to chemical means of attenuation. Killed *L. intracellularis* vaccines are also prepared using the cultivation methods of the invention. According to a particularly preferred embodiment, the bacteria are continuously cultured for at least about 6 to 8 months while being passaged at least about 7 to 12 times to produce an attenuated strain for use as a vaccine. The attenuated bacteria is then admixed with a pharmaceutically acceptable carrier and administered to an animal in an effective amount to produce an immune response. We have deposited the currently preferred attenuated strain (N343NP40wk) in the American Type Culture Collection.

The invention also provides a method for determining the presence of antibodies that specifically react with *L. intracellularis* bacteria in a biological sample by harvesting at least a portion of the cultivated *L. intracellularis* bacteria, contacting a biological sample from an animal with harvested *L. intracellularis* bacteria or a component thereof under conditions whereby antibody present in the biological sample reacts with the *L. intracellularis* or component, and determining if an antibody-antigen reaction has occurred.

Additional features and advantages of the invention will be set forth in the description which follows and will be apparent from the description or may be learned by practice of the invention.

DESCRIPTION OF THE PREFERRED EMBODIMENTS

As used herein, the term "*L. intracellularis*" means the intracellular, curved, gram-negative bacteria described in detail by C. Gebhart et al., Int'l. J. of Systemic Bacteriology, Vol. 43, No. 3, 533–38 (1993) and S. McOrist et al. Int'l. J. of Systemic Bacteriology, Vol. 45, No. 4, 820–25 (1995) (each of which is incorporated herein by reference in its entirety) and includes, but is not limited to, the bacteria deposited as ATCC 55672 in the American Type Culture Collection, Rockville, Md; the bacteria deposited as NCTC 12656 and 12657 in the National Collection of Type Cultures, Colindale, London; the causative bacteria which can be obtained from PPE infected swine or other animals throughout the world given the knowledge in the art and the teachings herein; and variants or mutants of any of the above bacteria, whether spontaneously or artificially obtained.

As used herein, the term "attenuated strain" means any *L. intracellularis* strain that is prepared according to the cultivation and passaging techniques taught herein to achieve avirulence while maintaining immunogenic properties when administered to a host animal. As demonstrated below, various different *L. intracellularis* strains have been cultivated and attenuated according to the present teachings to obtain attenuated immunogenic strains having efficacy as vaccines in swine and other animals susceptible to *L. intracellularis* infection.

The attenuated strains of the invention are expected to have utility as immunogens in antimicrobial vaccines for animals, including birds, fish, cattle, swine, horses, mammals and primates in general, and humans. Such vaccines can be prepared by techniques known to those skilled in the art, given the teachings contained herein. Such a vaccine would comprise an immunologically effective amount of the attenuated strain in a pharmaceutically acceptable carrier. The vaccine could be administered in one or more doses. An immunologically effective amount is determinable by means known in the art without undue experimentation, given the teachings contained herein. The amount of avirulent bacteria should be sufficient to stimulate an immune response in disease-susceptible animals while still being avirulent. This will depend upon the particular animal, bacteria, and disease involved. The recommended dose to be administered to the susceptible animal is preferably about $10^3$ to $10^9$ bacteria/Kg of body weight and most preferably about $10^5$ to $10^7$ bacteria/Kg of body weight. The carriers are known to those skilled in the art and include stabilizers and diluents. Such a vaccine may also contain an appropriate adjuvant. The vaccines of the invention may be used in combination with other vaccines, for example, as a diluent of another lyophilized vaccine, or combined before lyophilization with another vaccine. The vaccine preparations may also be desiccated, for example, by freeze drying for storage purposes or for subsequent formulation into liquid vaccines.

Accordingly, the invention also comprises a method for inducing an immune response to virulent, wild-type *L. intracellularis* bacteria in an animal host for the purpose of protecting the host from such bacteria. The method comprises administering an immunologically effective amount of the attenuated bacteria or killed bacteria of the invention to the host and, preferably, administering the vaccine of the invention to the host.

As used herein, the term "large-scale cultivation" means a level of cultivation of *L. intracellularis* greater than approximately 2.0 to 3.0 liters and includes production on a scale of 100 liters or more. "Cultivation" as used herein, means the process of promoting the growth, reproduction and/or proliferation of *L. intracellularis*.

In practicing the cultivation method of the invention, culture cells may first be inoculated with an inoculum comprising *L. intracellularis* bacteria so as to infect the cells with the bacteria. Numerous cell lines can be used in practicing the invention, including, but not limited to, IEC-18 (ATCC 1589)—rat intestinal epithelial cells, HEp-2 (ATCC 23)—human epidermoid carcinoma cells, McCoys (ATCC 1696)—mouse (nonspecified) cells, MDCK (ATCC 34)—Madin-Darby canine kidney cells, BGMK (Biowhittaker #71-176)—buffalo green monkey kidney cells, and swine intestinal epithelium cells. The preferred culture cells are HEp-2, McCoys or IEC-18 cells. Alternatively, the bacteria may be cultivated in a cell free system so long as the bacteria are maintained at the appropriate dissolved $O_2$ concentration as taught herein.

If culture cells are used, prior to being inoculated, the cells are preferably but need not be in the form of a monolayer. To form a monolayer, the cells may be seeded into conventional flasks. Each flask is generally seeded with between about $1 \times 10^5$ cells to about $10 \times 10^5$ cells per 25 cm$^2$ flask mixed with growth media. The growth media may be any media for cell cultivation which includes a nitrogen source, necessary growing factors for the chosen culture cells, and a carbon source, such as glucose or lactose. The preferred media is DMEM with 2–5% fetal bovine serum, although various other commercially available media may be used with good results.

We have found that successful cultivation of *L. intracellularis* is enhanced by maintaining the culture cells in a constant state of growth. Therefore, the culture cell monolayer should be at about 20 percent to about 50 percent confluency at the time of inoculation. Preferably, the cells should be at about 30 percent to about 40 percent confluency at the time of inoculation, with about 30 percent confluency being most preferred.

The inoculum may be a pure culture of *L. intracellularis* obtained, for example, from ATCC deposit 55672, NCTC deposits 12656 or 12657, or from infected swine or other animals using the isolation and purification teachings discussed herein.

According to one embodiment, the inoculum for practicing the invention is an intestinal homogenate prepared by scraping the mucosa off of the ileum of a swine or other animal infected with PPE. When preparing an intestinal homogenate, ileal sections selected for culture should show severe lesions with gross thickening of the gut. Due to the fragile nature of the bacteria, samples should preferably be stored at −70° C. as quickly as possible after necropsy. An antibiotic to which *L. intracellularis* is resistant such as Vancomycin, Amphotericin B or members of the aminoglycoside group of antibiotics, including Gentamicin and Neomycin, to name a few, is preferably added to the inoculum to suppress contaminating bacteria while permitting *L. intracellularis* growth. Whether the inoculum is a pure culture or an intestinal homogenate, inoculation of the culture cells can be performed by various techniques known in the art given the teachings herein.

The bacteria and/or inoculated culture cells are then incubated under a reduced dissolved $O_2$ concentration. At dissolved oxygen concentrations greater than 18% *L. intracellularis* growth is less than optimal with cessation of growth eventually occurring at oxygen concentrations outside this range. Preferably, the inoculated culture cells are incubated in a dissolved oxygen concentration in the range of from about 0% to about 10%. More preferably, the cells are incubated in an oxygen concentration in the range of from about 0% to about 8%, with an oxygen concentration of about 0% to about 3.0% being most preferred.

The proper concentration of carbon dioxide is also important to the proper growth of L. intracellularis. At carbon dioxide concentrations greater than 10% and less than 4%, non-optimum growth occurs with cessation of growth eventually occurring at carbon dioxide concentrations outside this range. Preferably, the carbon dioxide concentration is in the range from about 6% to about 9%, with a carbon dioxide concentration of about 8.8% being most preferred.

In addition, the cells are preferably incubated at a hydrogen concentration in the range from about 73% to about 94%. Nitrogen may be used in place of some or all of the hydrogen present. According to a particularly preferred embodiment, the cells are incubated in about 0–8.0% $O_2$, about 8.8% $CO_2$, and about 83.2% $H_2$.

Inoculated cells may be incubated in a dual gas incubator or other gas chamber which contains the proper oxygen and carbon dioxide concentrations and which allows the cells to be suspended during incubation. The chamber should comprise a means for maintaining the inoculated cells in suspension, and a gas monitor and supply source to supply and maintain the proper gas concentrations. The incubation temperature should be in the range of from 30° C. to 45° C. and is more preferably in the range of from about 36° C. to about 38° C. Most preferably, the temperature is about 37° C. The necessary equipment for the cultivation and attenuation methods of the invention is readily available to those of ordinary skill in the art given the teachings herein. One example of equipment suitable for carrying out the present invention is a dual gas incubator, e.g., model 480 available from Lab-Line, Melrose Park, Ill., in conjunction with spinner flasks to maintain the cells in suspension. The presently preferred equipment comprises a fermentor, bioreactor or rotary shaker containing at least about 2 litres media and capable of maintaining the culture cells in suspension via sparging gas of the appropriate concentration, or other means of mechanical agitation, and continuously monitoring dissolved $O_2$ levels in the media. New Brunswick, Braun and other companies make suitable fermentors and bioreactors for this purpose.

By maintaining the innoculated cells in a suspended state during incubation, maximum growth of the cells, and hence L. intracellularis, is achieved by increasing each individual cell's exposure to growth media and the proper mixture of oxygen and carbon dioxide. The culture cells can be agitated and maintained in suspension by a variety of methods known in the art, including, for example, culture flasks, roller bottles, membrane cultures and spinner flasks. The cells may be kept in suspension during incubation by incubating the cells in a spinner flask inside a dual gas incubator or similar apparatus. The term "spinner flask", as used herein, means a flask or other container which employs a paddle, propeller or other means to agitate the culture and keep the cells contained therein in suspension.

In a particularly preferred embodiment of the invention, the inoculated cells are incubated until the cells reach confluency and then the cells are placed in a spinner flask containing growth media and incubated in a dual gas incubator while spinning the flask. Preferably, the inoculated cells are scraped into the spinner flask. This can be achieved by a variety of methods known in the art such as using a cell scraper to detach the cells. Once the cells are introduced into the spinner flask, the paddle of the spinner flask is typically rotated in the range of from about 30 to about 60 rpm in order to maintain the infected cells in suspension.

A portion of the cultivated L. intracellularis is then passaged to fresh culture cells to increase the production of L. intracellularis bacteria. The term "passaging" or variations thereof herein means the process of transferring a portion of the cultivated L. intracellularis to fresh culture cells in order to infect the fresh cells with the bacterium. The term "fresh", as used herein, means cells which have not yet been infected by L. intracellularis. Preferably such cells are, on the average, no more than approximately one day old.

The passage of L. intracellularis in suspension cultures may be accomplished by removing a portion of the original culture and adding it to a new flask containing fresh culture cells. If the original culture has a high number of bacteria/ml, for example, greater than about $10^4$ bacterial/ml, it is preferable to add between about 1 to 10% (volume to volume) of culture from the infected flask to a new flask containing fresh cells. This is preferably done when 50–100% of the cells are infected. If fewer than 50% of the cells are infected, passaging is preferably accomplished by splitting the culture 1:2 into a new flask and scaling-up the volume by adding fresh media. In either case, cell lysis and other steps are not required, in direct contrast to the passage of monolayer cultures, as in the prior art.

After sufficient growth of the culture cells and subsequent infection by L. intracellularis at greater than about 70% cell infectivity, as determined by IFA, $TCID_{50}$ or other comparable method, at least a portion of the cultivated L. intracellularis bacteria is then harvested. The harvesting step may be performed by separating the bacteria from the suspension by various techniques known to those of ordinary skill in the art, given the teachings herein. Preferably, the L. intracellularis bacteria is harvested by centrifuging the contents of all or a portion of the suspension to pellet the culture cells, resuspending the resulting cell pellets, and lysing the infected cells. Typically, at least a portion of the contents is centrifuged at about 3000×g for about 20 minutes in order to pellet the cells and bacteria. The pellet may then be resuspended in, for example, a sucrose-phosphate-glutamate (SPG) solution and passed approximately four times through a 25 gauge needle in order to lyse the cells. If further purification is desired, the samples can be centrifuged at about 145×g for about five minutes to remove cellular nuclei and debris. The supernatant may then be centrifuged at about 3000×g for about twenty minutes and the resulting pellet resuspended in an appropriate diluent, such as SPG with fetal bovine serum (to prepare harvested bacteria suitable for freezing or use as an inoculant) or growth media (to prepare harvested bacteria more suitable for passaging to fresh cells).

As previously mentioned, effective growth of L. intracellularis for large-scale production is enhanced by keeping the tissue cells actively growing. With monolayers, when cultures become confluent the rate of cell division decreases substantially. Attempts to grow L. intracellularis on monolayer tissue cultures have had limited success and scale-up has not been possible. However, using suspension cultures greatly facilitates keeping the cells actively growing and permits continuous culture expansion and scale-up. Using a fermentor and between about 0–3% dissolved $O_2$ as explained above, we have been able to grow up to $10^8$ bacteria/ml. We have also been able to keep the cultured bacteria actively growing for many months and expect to be able to do so indefinitely.

Prior to the instant invention, it was generally believed that cells must be attached to a surface in order to be infected by L. intracellularis. The cell suspensions of the instant invention are unique and contradict this theory. When using McCoys or IEC-18 cells, it is preferable to add gelatin, agarose, collagen, acrylamide or silica beads, such as Cultisphere-G porous microcarriers manufactured by HyClone Laboratories, Logan, Utah, along with the growth media. However, HEp-2 cells and others do not require microcarriers according to the cultivation method of the invention. This provides an especially advantageous and economical route for large-scale cultivation.

For culture maintenance purposes, with HEp-2 cultures, preferably 25–50% of the culture is removed and replaced with fresh media at weekly intervals. For cell cultures with microcarriers or beads, preferably 25–50% of the culture is removed and replaced with fresh microcarriers or beads and fresh media 1–2 times weekly. For scale-up purposes, an additional 25–50% of media, or media with microcarriers, may be added to the culture.

Depending upon the rate at which the culture cells become infected, passage to fresh cells generally occurs between about every 2 to about 5 weeks. Assuming that the culture cells become at least 70% infected within 2–3 weeks, preferably passage occurs between about every 3 to 4 weeks.

The present invention also provides vaccines and methods for producing vaccines against *L. intracellularis*. According to a particularly preferred embodiment, after maintaining the infected cells in suspension for an extended time (for example, 6–8 months), at least a portion of the cultivated *L. intracellularis* bacteria are harvested and monitored for potential attenuation. Such monitoring is preferably accomplished by host animal or animal model challenges to select for an attenuated strain. Such attenuated strains are used in vaccines according to the methods taught herein. The attenuated *L. intracellularis* vaccines according to the present invention have shown efficacy against *L. intracellularis* infection in a variety of animals and are expected to be effective in humans as well.

The present invention allows rapid culture expansion, an increase in yields of 100–1000 fold, and reduced cost. As a result, the abundant supply of *L. intracellularis* bacteria produced according to the cultivation method of invention is readily attenuated for vaccine production purposes. Attenuation is difficult in monolayer cultures due to the low yield of bacteria produced using conventional monolayer growing techniques. In contrast, the method of growing *L. intracellularis* of the present invention greatly increases the ease, speed, and number of bacterium available for this purpose. The more cells and cell divisions which occur, the greater the level of mutations occurring which are advantageous in vaccine development. Growth in suspensions according to the invention increases the expression of important immunogens controlled by environmentally regulated genes and their expression products.

The resulting attenuated strains can be cultivated in tissue culture monolayers as described in Example 1 below, but are preferably cultivated in suspension cultures according to the method of the invention. Other means of attenuation can include chemical attenuation by the use of, for example, N-methyl nitrosoguanadine and others known in the art. Whether by multiple passage or chemical means, an attenuated *L. intracellularis* is produced and selected for vaccine preparation.

According to one vaccine embodiment of the invention, the antigen is harvested by centrifugation or microfiltration as described above. The antigen is then standardized at a defined level based on the optimum host animal immune response, determined by a dose titration in the host animal species. The bacteria may be inactivated by prolonged exposure, e.g., one week, to ambient $O_2$ levels, or by using 0.3% formalin or other inactivating agent to prepare a killed vaccine. The antigen is then incorporated into a suitable adjuvant, such as aluminum hydroxide or mineral oil to enhance the immune response. The antigen is then used to vaccinate the host via intramuscular or subcutaneous injection, in the case of pigs at about 3–4 weeks of age, with a booster dose if necessary.

Alternatively, according to a particularly preferred vaccine embodiment using the cultivation methods previously described, the bacteria are serially passaged to induce and select for an attenuated, avirulent live culture. The culture is tested in the host animal (after preferably at least 6 to 8 months or more of growth in the suspension culture) for signs of attenuation. The culture is harvested as described earlier and diluted. Pigs, for example, are orally vaccinated with $1 \times 10^5$ to $1 \times 10^6$ bacteria. About twenty-eight days after vaccination, the pigs are orally inoculated with about $1 \times 10^7$ organisms from a less passaged (about 30 to 45 days old) virulent culture of *L. intracellularis*. The infected animals are necropsied 21 days after challenge and the small intestines observed for gross lesions as well as microscopic lesions. PCR and fluorescent antibody should also be performed. About eighty percent of the control animals will show gross or microscopic lesions and test positive for the presence of *L. intracellularis* in the mucosal cells of the intestines using either PCR or FA testing methods. Vaccinated animals will have normal mucosal surfaces as determined by histological observations and will be negative by PCR testing.

Generally, an attenuated immunogenic *L. intracellularis* strain is produced after continuous culture for between at least about 150 and 250 days, during which time the culture is passaged at least about 7 to about 12 times. Other attenuated cultures may be produced by varying these figures so long as the monitoring and selection methods taught herein are employed.

A vaccine is then prepared comprising an immunologically effective amount of the attenuated *L. intracellularis* in a pharmaceutically acceptable carrier. The combined immunogen and carrier may be an aqueous solution, emulsion or suspension. An immunologically effective amount is determinable by means known in the art without undue experimentation given the teachings contained herein. In general, the quantity of immunogen will be between 50 and 500 micrograms, and preferably between $10^7$ and $10^9$ $TCID_{50}$, when purified bacteria are used.

The vaccines according to the invention are generally administered to susceptible animals, preferably swine, in one or more doses. The live or killed vaccine may be administered 1 or 2 times at 2 week intervals. For the attenuated, live vaccines, one dose is preferred. The preferred routes of administration of live attenuated strains are oral or intranasal, but intramuscular or subcutaneous injection may also be used. The intramuscular and subcutaneous injection routes are most preferred for the killed vaccine.

Effective diagnosis of PPE has also been hindered by the time required to culture the causative bacteria. As a result of the present invention, development of diagnostic tools promoting rapid and accurate assays for the presence of *L. intracellularis* in biological samples taken from swine and other animals susceptible to PPE is now possible.

The *L. intracellularis* bacteria grown according to the method of the instant invention, or components derived from such bacteria, can be used as an antigen in an ELISA or other immunoassay, such as an immunofluorescent antibody test ("IFA"), to detect antibodies to *L. intracellularis* in the serum and other body fluids of animals suspected of being infected with the bacteria. The presently preferred immunoassay is an IFA as described in the example below. Alternatively, the bacteria grown according to the invention can be used in a Western Blot assay.

The preferred ELISA protocol according to this embodiment of the invention is as follows:

1. Add 0.1 ml/well antigen diluted in coating buffer. Incubate for 18 hours at 4° C.
2. Wash 3 times with PBS.
3. Add 0.25 ml of blocking buffer to each well of plate. Incubate 1 to 2 hours at 37° C.
4. Wash 3 times with wash buffer.
5. Dilute serum in blocking buffer and add 0.1 ml to the first wells of plate. Make serial 1:2 dilutions across the plate. Incubate for 1 hour at 37° C.
6. Wash 3–5 times with wash buffer.
7. Dilute conjugate in blocking buffer and add 0.1 ml to wells of plate and incubate for 1 hr at 37° C.
8. Wash 3–5 times with wash buffer.
9. Add substrate.
12. Measure absorbance of light with a spectrophotometer.
13. Wells in which antigen was not added are used as blanks.
14. Positive and negative control pig serum should also be used with each test.

The preferred Western blot protocol is as follows:

1. Run antigen on 12% SDS-PAGE and transfer to nitrocellulose membrane.
2. Place membrane in blocking buffer for 2 hr.
3. Remove blocking buffer and rinse with PBS for 1 minute.
4. Dilute serum in blocking buffer and add to membrane. Incubate for 2 hours at room temperature.
5. Wash 3 times with wash buffer (5 minutes for each wash).
6. Dilute conjugate in blocking buffer and add to membrane. Incubate for 1 hr. at room temperature.
7. Wash 3 times with wash buffer.
8. Add substrate for 10 minutes or until strong banding occurs.
9. Rinse with PBS.
10. Air dry and store in the dark.

The present invention is further described in the following examples which are provided for illustrative purposes only and are not to be construed as limiting.

EXAMPLE 1

Isolation of *L. intracellularis* from the Intestines of American Pigs with Porcine Proliferative Enteropathy Materials and Methods:
Selection of Inoculum Samples:

Sample N24912 was obtained from a herd on a farm in Iowa in which fifteen of 300 five month old finisher pigs were observed to have persistent bloody stools despite penicillin treatment. Upon necropsy of the pigs, the intestine (ileum) had a thickened mucosa. Histopathology examinations with silver stains demonstrated the presence of curved intracellular bacteria and crypt enterocyte hyperplasia confirming the diagnosis of PPE. Sample N72994 was obtained from a 1.5 year old second litter SPF sow on a farm in Minnesota. The herd size was between 70–80 sows and antibiotic treatment is unknown. Upon necropsy, the mucosa of the ileum was thickened with some hemorrhage. Giminez staining of the mucosa demonstrated many curved bacteria. Sample N101494 was obtained from a 12 week old pig from an Indiana farm with 600 furrow to finish sows. The pig was treated with Tylan injectable upon the onset of bloody diarrhea, but the animal died soon after treatment.

Preparation of Pig Derived Bacterial Inocula:

Intestinal samples were kept at −70° C. The intestines were opened and washed with phosphate buffered saline (PBS). One gram samples of mucosa were scraped into sodium potassium glutamate (SPG) and homogenized for 30 seconds with 4.0 ml 1% Trypsin (JRH Biosciences, Lenexa, Kans.) in SPG. The suspensions were incubated for 35 minutes at 37° C. Ten ml SPG/10% fetal calf serum (FCS) (JRH Biosciences, Lenexa, Kans.) was added and the samples were ground in a tissue grinder for 1 minute. Ten ml SPG/10% (FCS) was added and filtered once through filterpaper (Whatman 113V; Whatman Labsales, Hillsboro, Oreg.) and sequentially through 5.0, 1.0, and 0.65 micron membrane filters. Filtrates were aliquoted and frozen at −70° C. in 1.0 ml aliquots. The mucosa was smeared onto a slide for Giminez stain. Separate smears of filtrates were stained by IFA using a specific monoclonal antibody for *L. intracellularis*. S. McOrist et al., Vet. Rec. 121:421–422 (1987) (incorporated by reference herein in its entirety).

Cell Culture:

IEC-18 cells (Rat intestinal epithelial cells, ATCC CRL 1589) were grown in DMEM (JRH Biosciences, Lenexa, Kans.) with L-glutamine and 10% FCS and routinely passaged by trypsin weekly. Cell monolayers were grown at 37° C. in air with 5% $CO_2$.

Infection of Cell Culture:

IEC-18 cells were seeded at $1.25 \times 10^5$ cells in 25 $cm^2$ flasks and at comparable rates in chamberslides (Nunc, Inc., Naperville, Ill.), incubated 24 hours, then media removed. Frozen pig-derived bacterial isolates were quickly thawed and diluted in DMEM/7% FCS with Vancomycin (100 $\mu$g/ml) and Amphotericin B (2.0 $\mu$g/ml) at ratios of 1.0 ml homogenate to 15 ml media and added to the monolayers. Monolayers and bacterial suspensions were centrifuged for 30 minutes at 2000 g and transferred to anaerobic jars. The jars were evacuated and the gas was replaced with hydrogen and carbon dioxide to give a mixture of 8.0% $O_2$, 10% $CO_2$, and 82% $H_2$. The cultures were incubated for 3 hours at 37° C. then refed with DMEM/7% FCS with L-glutamine, Vancomycin (100 $\mu$g/ml), Neomycin (50 $\mu$g/L), and Amphotericin B (2.0 $\mu$g/ml). Cultures were replaced in the anaerobic jars and incubated for 6 days with media changes every 2 days.

Passage of *L. intracellularis*:

*L. intracellularis* bacteria were passed by cell lysis using potassium chloride as described previously in G. Lawson et al., J. Clin. Microbiol., 31:1136–1142 (1993) (incorporated by reference herein in its entirety) then added to fresh IEC-18 monolayers. Media was poured off the monolayers and 0.1% KCl was added and the cells incubated for 10 minutes at 37° C. The KCl was removed and SPG/10% was added and the monolayers detached mechanically with a cell scraper. The cells were lysed by passing 3 times through a syringe with a 21 gauge needle. Cell nuclei were removed by centrifugation at 100×g for 5 minutes and the bacterial suspension in the supernatant fluid added to fresh 1 d monolayers of IEC-18 cells.

Monitoring Infection of Cell Cultures:

Infection was monitored by fixing the cells on chamberslides with cold acetone/methanol for 5 minutes. Staining was carried out by immunofluorescence and immunoperoxidase methods. Both methods employed a mouse monoclonal antibody (as described in S. McOrist et al., Vet. Rec. 121:421–422 (1987)) as the primary antibody and either anti-mouse immunoglobulin G-fluorochrome conjugate (fluorescein isothiocyonate; Organon Teknika Corporation, Durham, N.C.) or peroxidase conjugate (goat anti-mouse immunoglobulin G; Kirkegaard and Perry Laboratories, Inc., Gaithersburg, Md.). Quantitation of bacteria was accomplished by counting the number of specifically stained bacteria within cells on each slide.

Polymerase Chain Reaction:

Sample inocula and passaged bacteria were incorporated as template DNA into PCR using the sample preparation method, primers, and cycle parameters as described by Jones et al., J. Clin. Microbiol., 31:2611–2615 (1993) and McOrist et al., Vet. Microbiol. 1–8 (1994) (each of which are incorporated by reference herein in their entirety). Cycle parameters were 93° C. for 5 minutes, 55° C. for 45 seconds, and 72° C. for 45 seconds for the first cycle. Thirty-three cycles were performed at the previously mentioned temperatures for 45 seconds per temperature, as well as one cycle at 93° C. for 45 seconds, 55° C. for 45 seconds, and 72° C. for 2 minutes. Positive inocula only were used to inoculate IEC-18 cells. PCR was also performed for the monitoring of passage material to confirm infections. DNA produced by PCR was submitted to the Iowa State University Nucleic Acid Facility for sequencing. Results of the sequencing were compared to sequences produced by Gary F. Jones as reported in his Ph.D. thesis, University of Minnesota, Minneapolis, Minn. (June, 1993).

Results:

Selection of Inoculum Samples:

Pig number N24912 and N72994 had severe PPE with bloody intestinal contents and thickened mucosa. N101494 had severe PPE and severe hemorrhage resulting in a large blood clot in the intestinal lumen. Giminez staining of the mucosal smears demonstrated large numbers of curved or S-shaped bacteria. IFA stains revealed large numbers of brightly fluorescing bacteria in pig-derived bacterial inocula.

Monitoring Infection of Cell Cultures:

Inoculated monolayers were monitored by light microscopy throughout the growth cycle and little morphological change of the cells was observed. Uninfected monolayers grown under reduced oxygen tension (8% $O_2$) had similar morphology.

Immunofluorescence and immunoperoxidase stained infected cultures demonstrated large numbers of curved or S-shaped specifically stained bacteria apparently within cells. The monolayers did not have confluent infection. Infected cells were often closely associated with infected foci of 1–10 cells. Heavily infected cells (i.e., cells with 30 or more bacteria) were also seen in association with cells with fewer than 30 bacteria. Bacterial numbers peaked at or about 6 days. Infection was dependent on specific growth conditions. The bacteria were successfully passaged by the cell lysis procedure described herein. Centrifugation of newly inoculated cells was not necessary but enhanced the numbers of infected cells. Centrifugation also decreased contamination by allowing cells exposed to infection with antibiotic-free media to be refed at 3 hours with antibiotic containing media. Reducing FCS from 10% to 7% in the media was necessary to slow the growth of the IEC-18 cells allowing the bacteria to proliferate to higher numbers before monolayers became confluent.

Polymerase Chain Reaction:

PCR of chromosomal DNA generated a 319 bp fragment (including primers) from all isolates. A fragment of appropriate size was visually compared to a known positive sample generated by McOrist et al. (1994) using PCR. Sequence analysis of the PCR products of N24912, N72994, and N101494 confirmed a close homology (97–99%) to the p78 sequence determined by Jones (1993).

EXAMPLE 2

Growth of L. intracellularis in Suspension Cultures of HEp-2 Cells

Preparation of Intestinal Homogenates for Inoculum:

Intestinal homogenate was prepared by scraping the mucosa off of 6.0 to 8.0 cm of ileum from the intestinal samples of Example 1. Trypsin (1%) was added to the scraped mucosa and the samples were homogenized briefly, then incubated for 35 minutes at 37° C. Ten ml SPG/10% FBS was then added and the samples were ground in a tissue grinder. Another 10 ml SPG/10% FBS was added. The homogenates were passed through a Whatman V113 filter and then sequentially through 5.0, 1.0, and 0.65 $\mu$m filters. The samples were dispensed into 1 ml aliquots and frozen at $-70°$ C.

Infection of Cell Culture:

Method A:

Tissue cells were seeded at $1\times10^7$ cells in 50 ml DMEM/10% FBS in a 100 ml spinner flask. The cultures were incubated 24 hr., then Vancomycin and fungizone were added. One vial of frozen intestinal homogenate was quickly thawed and diluted in 3.0 ml DMEM/5% FBS with Vancomycin (100 $\mu$g/ml) and Amphotericin B (2.0 $\mu$g/ml). The sample was passed through a 0.65 $\mu$m filter and added to the flask. The culture was placed in a gas chamber, evacuated, and regassed with hydrogen and carbon dioxide to give a mixture of 8.0% $O_2$, 8.8% $CO_2$, and 83.2% $H_2$. The cultures were incubated for 3 hours at 37° C. and then Neomycin and Gentamycin were added. The culture was refed at 24 hours with DMEM/5% FBS with L-glutamine, Vancomycin (100 $\mu$g/ml), Neomycin (50 $\mu$g/L), Gentamycin (50 $\mu$g/L) and Amphotericin B (2.0 $\mu$g/ml).

Method B:

Two 25 $cm^2$ conventional flasks were seeded with $1.25\times10^5$ HEp-2 cells in DMEM/10% FBS and allowed to grow 18–24 hours. The cells were at 30% confluency at time of inoculation. The inoculum was diluted in DMEM/5% FBS. When the inoculum is from an intestinal homogenate, the media also contained Vancomycin (100 $\mu$g/ml) and Amphotericin B (2.0 $\mu$g/ml). The cultures were placed in a gas chamber, evacuated, and regassed with hydrogen and carbon dioxide to give a mixture of 8.0% $O_2$, 8.8% $CO_2$, and 83.2% $H_2$. The cultures were incubated for 3 hours at 37° C. then Neomycin and Gentamycin were added. The culture was refed at 24 hours with DMEM/5% FBS with L-glutamine, Vancomycin (100 $\mu$g/ml), Neomycin (50 $\mu$g/L), Gentamycin (50 $\mu$g/L), and Amphotericin B (2.0 $\mu$g/ml). No antibiotics were required when the inoculum was a pure culture. The cultures were incubated for 6 days or until confluency. The cells were scraped from the flasks and added to a 100 ml spinner flask containing 50 ml DMEM/5% FBS.

The culture was diluted 1:2 at weekly intervals by either harvesting one half of the culture and adding fresh media or by passing into a larger spinner flask and adding more media.

Passage of the Culture:

The culture was passed to fresh HEp-2 cells by seeding new HEp-2 cells at $1\times10^7$ into DMEM/5% FBS. The new culture was allowed to incubate overnight at 8.0% $O_2$, 8.8% $CO_2$, and 83.2% $H_2$. The new culture was then inoculated with infected culture and incubated at reduced $O_2$ concentrations as previously stated. Inoculum amounts were dependent on the degree of infection of the original culture.

Harvesting and Storage of Cultures:

The cultures were harvested by collecting the desired amount of culture while centrifuging at 3000×g for 20 minutes. The pellet was resuspended in Sucrose-Phosphate-Glutamate (SPG) solution and passed 4 times through a 25 gauge needle. The cultures were aliquoted and frozen at −70° C. For further purification, the sample was centrifuged at 145×g for 5 minutes to remove the cellular nuclei and debris. The supernatant was then centrifuged at 3000×g for 20 minutes. The pellet was then resuspended in diluent.

Estimation of Viable L. intracellularis in Tissue Culture:

Quantitation of viable L. intracellularis was accomplished by determination of the Tissue Culture Infectious Dose 50 percent ($TCID_{50}$). This was done by removing 2.0 ml of culture to be tested and lysing the cells by passing through a 25 gauge needle 4 times. The sample was serially diluted 1:10 in DMEM/5% FBS containing Vancomycin (100 µg/ml) and Amphotericin B (2.0 µg/ml). The dilutions were added to a 96 well microtiter plate with 0.1 ml/well. The microtiter plates were seeded with HEp-2 cells at 1250 cells/well and grown 18–24 hours prior to infection. Between 3 wells/dilution and 6 wells/dilution were used. The plate was incubated for 6 days at gas concentrations of 8.0% $O_2$, 8.8% $CO_2$, and 83.2% $H_2$. The cells were fixed with cold 50% acetone and 50% methanol for 2 minutes. To the wells, 0.03 ml/well of anti-IS intracellularis monoclonal antibody (McOrist, 1994) diluted 1:2000 in PBS was added. The plate was incubated for 30 minutes at 37° C. and then washed 3 times with PBS. Anti-mouse FITC diluted 1:30 was added in the amount of 0.03 ml/well and incubated 30 minutes at 37° C. The plate was then washed 3 times with dd$H_2O$ and allowed to dry. Samples were observed on a fluorescent microscope and the $TCID_{50}$/ml was determined.

Results:

The $TCID_{50}$ results indicated that the cultures contained up to 1×10⁶ bacteria/ml. This was accomplished in 45 days. The culture volume was scaled-up to 3.0 litres in the same amount of time.

EXAMPLE 3

Growth of L. intracellularis in Suspension Cultures of McCoys Cells

Preparation of Intestinal Homogenates for Inoculum:

Intestinal homogenate was prepared as described in Example 2. A sample of L. intracellularis cultivated according to the method of the following example was deposited under the Budapest Treaty on May 19, 1995 in the American Type Culture Collection (ATCC), 12301 Parklawn Drive, Rockville, Md. U.S.A. 20852 and assigned accession number 55672.

Infection of Cell Culture:

Two 25 cm² conventional flasks were seeded with 1.25× 10⁵ McCoys cells in DMEM/10% FBS and allowed to grow 18–24 hours. The cells were at 30% confluency at time of inoculation. The inoculum was diluted in DMEM/5% FBS. When the inoculum is from an intestinal homogenate, then the media also contained Vancomycin (100 µg/ml) and Amphotericin B (2.0 µg/ml). The cultures were placed in a gas chamber, evacuated, and regassed with hydrogen and carbon dioxide to give a mixture of 8.0% $O_2$, 10% $CO_2$, and 82% $H_2$. The cultures were incubated for 3 hours at 37° C., then Neomycin and Gentamycin were added. The culture was refed at 24 hours with DMEM/5% FBS with L-glutamine, Vancomycin (100 µg/ml), Neomycin (50 µg/L), Gentamycin (50 µg/L), and Amphotericin B (2.0 µg/ml). No antibiotics were required when the inoculum was a pure culture. The cultures were incubated for 6 days until confluency. The cells were scraped from the flasks and added to a 100 ml spinner flask containing 50 ml DMEM/2% FBS and 0.05 g Cultisphere-G Microcarriers. The flasks were stirred at 40–50 rpms.

The culture was diluted 1:2 every 2–3 days by either harvesting one half of the culture and adding fresh media and Cultisphere-G beads or by passing the culture into a larger spinner flask and adding more media and Cultisphere-G beads. The final concentration of beads in the culture was about 0.001 g beads/ml.

Passage of the Culture:

The culture was passed to fresh McCoys cells by seeding 1×10⁷ new McCoys cells into DMEM/2% FBS and 0.05 g Cultisphere-G beads. The new culture was allowed to incubate overnight at 8.0% $O_2$, 8.8% $CO_2$ and 83.2% $H_2$. The new culture was then inoculated with 25 ml of infected culture and incubated at reduced $O_2$ concentrations as previously stated.

Harvesting and Storage of Cultures:

The cultures were harvested by collecting the desired amount of culture and centrifuging at 3000×g for 20 minutes. The pellet was resuspended in SPG and passed 4 times through a 22 gauge needle. The cultures were aliquoted and frozen at −70° C. For further purification, the sample was centrifuged at 145×g for 5 minutes to remove the beads, cellular nuclei and debris. The supernatant was then centrifuged at 3000×g for 20 minutes. The pellet was then resuspended in diluent.

Estimation of Viable L. intracellularis in Tissue Culture:

Quantitation of viable L. intracellularis was determined as described in Example 2 using a 22 gauge needle to lyse the cells and using McCoys cells at 1250 cells/well to seed the microtiter plates.

Results:

The $TCID_{50}$ results indicated that the cultures contained up to 1×10⁶ bacteria/ml. This was accomplished in less than 1 month. The culture volume was scaled-up to 3.0 liters in the same amount of time.

EXAMPLE 4

Determining Infectious Dose of L. intracellularis Pure Cultures in Host Animals

Summary:

A thirty-one pig study was completed by infecting 6 week-old conventional pigs with pure cultures of L. intracellularis from sample N72994. The pigs were randomly divided into 4 groups and the groups were penned separately. Group 1 contained 7 pigs and was considered the negative control group dosed with uninfected tissue culture or nothing. The group 2 contained 8 pigs dosed with 10⁷ bacteria/pig. Group 3 had 8 pigs and was dosed with 10⁶ bacteria/pig. And, Group 4 contained 8 pigs receiving 10⁵ bacteria/pig.

Fecal swabs were collected on days 0, 7, 14, and 21, and 24 for PCR testing. On day 24, the pigs were necropsied and the ileum, jejunum, and the colon were collected for PCR testing, histopathology, and FA stains, all as described above.

PCR testing of the ileal mucosa revealed the presence of L. intracellularis in 100% of the high dose, 75% of the medium dose, and 50% of the low dose. Histopathology results indicated an increase of mononuclear cells in the lamina propria and submucosa of 88% of the high dose, 75% of the medium dose, and 88% of the low dose. Crypt hyperplasia was observed in 50% of the high dose, 63% of the medium dose, and 50% of the low dose. FA staining revealed *L. intracellularis* in tissue sections of the ileum, jejunum, and colon in 88% of the high dose, 63% of the medium dose, and 63% of the low dose. Control animal were negative for the presence of *L. intracellularis* via PCR, FA, and silver stains.

In conclusion, a pure culture was successfully used to infect and cause lesions of PPE. Koch's postulates were fulfilled by the identification and isolation of *L. intracellularis* from the infected animals.

In challenged animals 100% of the high dosed animals had confirmed recovery and identification via silver stains, FA, and PCR.

Materials and Methods:
Growth of Inoculum:

One 75 cm$^2$ conventional flask was seeded with 3.75×10$^5$ HEp-2 cells in DMEM/10% FBS and allowed to grow 18–24 hrs at 37° C. at 5% $CO_2$. (The cells were at 30% confluency at time of inoculation.) One vial of N72994 was diluted in 15 ml DMEM/5% FBS. The culture was placed in a gas chamber, evacuated, and regassed with hydrogen and carbon dioxide to give a mixture of 8.0% $O_2$, 8.8% $CO_2$ and 83.2% $H_2$. The culture was refed at 24 hr. with DMEM/5% FBS.

The cultures were incubated for 6 days, then the cells were scraped from the flasks and added to a 100 ml spinner flask containing 50 ml DMEM/5% FBS. The flask volume was scaled-up by doubling the media volume at weekly intervals. The culture was grown for 3 weeks in the spinner flask.

Harvesting Cultures:

The culture was harvested by centrifuging at 3000×g for 20 minutes. The pellet was resuspended in Sucrose-Phosphate-Glutamate solution (SPG) with 10% FBS and passed 4 times through a 25 gauge needle. Inoculum was diluted to the final volume in SPG/10% FBS and 1:10 dilutions were made.

The inoculum for the controls consisted of non-infected HEp-2 cells diluted to the same concentration of viable cells as the infected culture. The cells were harvested the same as the infected culture. The control pigs received a similar dose of cells as the high dose group.

Quantitation of *L. intracellularis:*

Quantitation of viable *L. intracellularis* was accomplished by determination of the Tissue Culture Infectious Dose 50 percent ($TCID_{50}$). This was done by removing 2 ml of culture to be tested and lysing the cells by passing through a 22 gauge needle 4 times. The sample was serially diluted 1:10 in DMEM/5% FBS containing Vancomycin (100 $\mu$g/ml) and Amphotericin B (2.0 $\mu$g/ml). The dilutions were added to a 96 well microtiter plate with 0.1 ml/well. The microtiter plates were seeded with HEp-2 cells at 2500 cells/well and grown 18–24 hours prior to infection. Twelve wells/dilution were used. The plate was incubated for 6 days at gas concentrations of 8.0% $O_2$, 8.8% $CO_2$ and 83.2% $N_2$. The cells were fixed with cold 50% acetone and 50% methanol for 2 minutes. To the wells, 0.03 ml/well of anti-*L. intracellularis* monoclonal antibody (McOrist, 1987) diluted 1:2000 in PBS was added. The plate was incubated for 30 minutes at 37° C. and then washed 3 times with PBS. Anti-mouse FITC diluted 1:30 was added at 0.03 ml/well and incubated 30 minutes at 37° C. The plate was washed 3 times with $ddH_2O$ and allowed to dry. Samples were observed on a fluorescent microscope and the $TCID_{50}$/ml was determined.

Animals:

Thirty-one mixed sex pigs six weeks of age from PIC× Lieske females and large white boars were provided by Dr. Kent Schwartz. The pigs were randomly distributed to 4 pens by weight on day 0.

Facility:

Four pens in a small nursery facility, each separated by at least 3 feet, were used to house the pigs. The pens had wire flooring and solid pen dividers. Heat was provided by a furnace with zonal supplemental heat by heatlamps. The temperature was maintained between 78° and 85° F. for the duration of the study.

Feed and Water:

A 19% protein, ground corn-soy diet, free of antibiotics, was provided ad libitum via stainless steel feeders. Water was provided ad libitum via nipple waterers.

Infection of Pigs:

On day 0, the pigs were weighed and blood samples collected via capillary tube placed in the retroorbital sinus. Serum was harvested and stored frozen at −20° C. Fecal swabs were also collected for PCR. The pigs were dosed with 10 ml inoculum given intragastrically via stomach tube.

| Treatment | No. pigs |
|---|---|
| Control - uninfected cells | 5 |
| Control - no treatment | 2 |
| High dose | 8 |
| Medium dose | 8 |
| Low dose | 8 |

The pigs were weighed and bled on days 0, 10, 17 and 24.

Polymerase Chain Reaction:

Infection of the pigs was monitored by PCR using primers and cycle parameters as described by Jones (1993). Fecal samples collected on days 0, 7, 14, 21, and 24 as well as mucosa of the intestines were checked by PCR.

Histopathology:

Sections of ileum, jejunum, and colon were formalin fixed, processed routinely, stained with Ilematoxylin and Eosin as well as silver impregnation and evaluated. Sections were also stained using monoclonal antibody specific for *L. intracellularis.*

Results:

Clinical Signs:

Clinical signs consisting of loose stools were first observed in the high dose group at 3 days. The signs peaked at 14 days and began to resolve thereafter.

Weight Gain:

Average daily weight gains were calculated showing that the high and medium dose groups had reduced weight gains compared to the control group. There was a dose titration effect in the weight gains when comparing the groups.

PCR:

Fecal shedding was not observed until 14 days. At 21 days, 37.5% of the high dose pigs were PCR positive in the feces. After necropsy, the mucosas of the ileums were checked by PCR with 100% positive in the high dose, 75% in the medium dose, 50% in the low dose and 0% in the controls.

Gross Lesions:

Gross lesions were found in 2 pigs of the high dose group (#50 and #202). The pigs had approximately 3 ft of thickening in the ileum with necrosis in #202.

Histopathology:

FA:

FA staining of sections of the ileum, jejunum, and colon revealed the presence of *L. intracellularis* in 87.5% of the high dose, 62.5% of both the medium and low doses and 0% in the controls.

Microscopic Lesions:

Lesions were observed in 100% of the high dose, 75% of the medium dose, 87.5% of the low dose and 14% in the controls. This was determined by the observation of increased mononuclear cells in the lamina propria and submucosa, often associated with hyperplasia of Peyer's Patchers. Crypt hyperplasia was also observed.

Silver Stain:

Silver staining of sections for the presence of intracellular, curved bacteria was also done. This demonstrated the presence of bacteria in 87.5% of the high dose, 62.5% in the medium dose, 87.5% in the low dose and 0% in the controls.

Discussion:

The pigs were successfully infected with pure cultures of L. intracellularis. At doses of $10^7$ bacteria, 100% of the pigs demonstrated infection by PCR and microscopic lesions. The severity of the lesions and the amounts of bacteria in the tissue sections were relatively low. This study is a satisfactory challenge model for L. intracellularis due to the presence of L. intracellurlaris and microscopic lesions in the pigs. Lesions may be improved with a second dose 7 days after the first dose.

Example 5

Hamster Vaccine Efficacy Experiment

Goal:

Evaluate a lab animal model for determining the safety and efficacy of an avirulent-live vaccine of L. intracellularis in hamsters.

Summary:

A 40 hamster study was completed by vaccinating 3 week-old hamsters with pure cultures of a high passage strain of L. intracellularis and challenging 22 days after vaccination with pure cultures of low passage virulent material. The hamsters were divided into 3 groups. Group A was vaccinated with 1 dose of L. intracellularis strain N72994 at day 0. Group B was designated the control group and was not dosed with a vaccine culture. Both groups were challenged with 2 doses of a pure culture of L. intracellularis strain N343 on days 22 and 25 post-vaccination. Group C was given challenge strain, N101494, to compare relative virulence to strain N343. Groups A and B contained 15 hamsters each and Group C contained 10 hamsters. Tissue Culture Infectious Dose 50% ($TCID_{50}$) results indicated that the hamsters were vaccinated with $10^5$ $TCID_{50}$/dose. The N343 challenge contained $10^{5.5}$ $TCID_{50}$/dose. The challenge dose for Group C was $10^{2.75}$ $TCID_{50}$/dose. Fecal swabs were collected on days 0, 7, 14, 21, 29, 36, and 43 for polymerase chain reaction (PCR) testing. On day 21, 5 animals were necropsied from Groups A and B each for PCR testing of the mucosas as well as FA, Hematoxalin and Eosin stains, and Silver stains of ileal sections to determine the persistence of colonization of the bacteria in the vaccinated hamsters. The remaining animals were necropsied 21 days post-challenge with similar testing.

PCR results indicated the presence of L. intracellularis in the intestinal mucosas of 100% of the Group A hamsters 21 days post-vaccination. Group B hamsters were all negative at 21 days post-vaccination. Twenty-one days post-challenge 50% of the hamsters were PCR positive in Group A 100% were positive in Group B. Histopathology of the sections indicated mild to severe lesions in 50% of animals in Group A and mild lesions in 50% in Group B 21 days post-challenge. No animals demonstrated lesions 21 days post-vaccination. Group C animals did not have lesions at 21 days post-challenge. FA and silver stains were not able to demonstrate the presence of L. intracellularis in any of the sections.

In conclusion, a 50% reduction of infection was observed in hamsters vaccinated with a high passage strain of L. intracellularis as demonstrated by PCR. The intestines were colonized by low numbers of intracellular organisms as demonstrated by the lack of observed organisms in FA and silver stained sections. Hamsters in Group C were unable to show infection throughout the study most likely due to the low dosage of bacteria.

Materials and Methods:

Hamster Description:

Forty 3 week old female hamsters from Harlan Sprague Dawley were used.

Growth of Inoculum:

Vaccine Culture:

A continuous culture of L. intracellularis grown in HEp-2 cells for 29 weeks was used. The culture was grown in a similar manner as stated in the challenge culture section except the culture is passed to new HEp-2 cells every 2–3 weeks.

Challenge cultures:

One 75 $cm^2$ conventional tissue culture flask was seeded with $3.75 \times 10^5$ McCoys cells in Dulbecco's Modified Eagle's Medium (DMEM) with 10% Fetal Bovine Serum (FBS) and allowed to grow 18–24 hrs at 37° C. with 5% $CO_2$. The media was removed from the cells and one vial of N343 MSC X diluted in 14 ml DMEM/2% FBS was added to the flask. The culture was placed in a gas chamber, evacuated, and regassed with hydrogen and carbon dioxide to give a mixture of 8.0% $O_2$, 8.8% $CO_2$ and 83.2% $H_2$. The culture was grown for 6 days, then the cells were scraped into a 100 ml spinner flask with 90 ml DMEM/2% FBS and 0.01 g of cultisphere-G beads. The culture was grown at the gas concentrations stated above. The flask volume was scaled-up by doubling the media volume at weekly intervals. The culture was grown for 25 days in the spinner flask to a final volume of 250 ml.

Strain N101494 was grown in the same manner as strain N343.

Harvesting Cultures:

Vaccine Culture:

The culture was harvested by centrifuging at 3000×g for 20 minutes. The pellet was resuspended in Sucrose-Phosphate-Glutamate solution (SPG) with 10% FBS and passed 4 times through a 25 gauge needle. Inoculum was diluted to the final volume (15 ml) in SPG/10% FBS.

Challenge Cultures:

The cultures were harvested by centrifuging at 3000×g for 20 minutes. The pellets were resuspended in Sucrose-Phosphate-Glutamate solution (SPG) with 10% FBS and passed 4 times through a 25 gauge needle. The inoculum were diluted to the final volume in SPG/10% FBS (20 ml for strain N343 and 10 ml for strain N101494).

Dosage of Hamsters:

Vaccine:

At day 0 all hamsters in Group A were orally vaccinated with 1 ml of the prepared vaccine.

Challenge:

Twenty-two days post-vaccination, 10 hamsters in Group A and 10 hamsters in Group B were orally dosed with 0.5 ml of challenge culture strain N343. Group C was challenged with 0.5 ml of challenge culture strain N101494.

Quantitation of IS Intracellularis:

Quantitation of viable IS intracellularis was accomplished by determination of the Tissue Culture Infectious Dose 50 percent ($TCID_{50}$). This was done by removing 2 ml of culture to be tested and lysing the cells by passing through a 22 gauge needle 4 times. The sample was serially diluted 1:10 in DMEM/5% FBS containing Vancomycin (100 ug/ml) and Amphotericin B (2.0 ug/ml). The dilutions were dispensed at 0.1 ml/well to a 96 well microtiter plate which was seeded with McCoys cells at 1250 cells/well and incubated 18–24 hours at 37° C. at 5% $CO_2$ prior to infection. Twelve wells/dilution were used. The plate was incubated for 6 days at gas concentrations of 8.0% $O_2$, 8.8% $CO_2$ and 83.2% $N_2$. On day 6, the cells were fixed with cold 50% acetone and 50% methanol for 2 minutes. To the wells, 0.03 ml/well of anti-IS intracellularis monoclonal antibody diluted 1:2000 in PBS was added. The plate was incubated for 30 minutes at 37° C. and then washed 3 times with PBS. Anti-mouse FITC diluted 1:30 was added at 0.03 ml/well and incubated 30 minutes at 37° C. The plate was washed 3 times with $ddH_2O$ and allowed to dry. Samples were observed on a fluorescent microscope and the $TCID_{50}$/ml was determined.

Monitoring Infection of Hamsters:

Infection of the hamsters was monitored by PCR using primers and cycle parameters as described by Gary Jones. Fecal samples were collected at 0, 7, 14, 21, 29, 36, and 43 days post-vaccination. After termination of the hamsters the mucosa of the intestines were also checked by PCR.

Histopathology:

Sections of ileum and colon were formalin fixed, processed routinely, stained with Hemtoxylin and Eosin and silver impregnation, and evaluated. The sections were also stained with a monoclonal antibody specific for *L. intracellularis*.

Average Daily Weight Gains:

Weights of the hamsters were collected 21, 28, 35, and 42 days post-vaccination to determine the average daily weight gains.

Results: Refer to Table Below.

$TCID_{50}$:

$TCID_{50}$ results indicated that the vaccine group (Group A) received $10^{4.86}$ $TCID_{50}$/hamster. Hamsters in Groups A and B were challenged with strain N343 and received $10^{5.5}$ $TCID_{50}$. Group C hamsters challenged with strain N101494 received $10^{2.75}$ $TCID_{50}$/hamster.

PCR:

PCR testing demonstrated the presence of *L. intracellularis* in 100% of the vaccinated hamsters that were necropsied 21 days post-vaccination. Testing 43 days post-vaccination demonstrated that 100% of the control hamsters and 50% of the vaccinated hamsters were infected with *L. intracellularis*. None of the hamsters challenged with N101494 were positive. Fecal shedding was not detected throughout the study in any of the hamsters.

Histopathology:

H & E stains revealed no histological lesions in all sections of hamsters necropsied 21 days post-vaccination. In sections harvested 43 days post-vaccination 50% of the Vaccine group had mild to severe lymphocytic enteritis and 50% of the control group had mild lymphocytic enteritis. No lesions were seen in the N101494 challenge group.

FA stains failed to demonstrate *L. intracellularis* in any of the hamsters 43 days post-vaccination.

Discussion:

A 50% reduction of infection was observed in hamsters vaccinated with a high passage strain of *L. intracellularis* as demonstrated by PCR.

| ID | Fecal PCR D0 | Fecal PCR d7 | Fecal PCR d14 | Fecal PCR d21 | Fecal PCR d29 | Fecal PCR d36 | Fecal PCR d43 | Mucosa PCR Day 21 | Mucosa PCR Day 43 | Microscopic Lesions HE stain | Silver | FA |
|---|---|---|---|---|---|---|---|---|---|---|---|---|
| A-1 | − | − | − | − | − | − | − | NA | + | Mild enteritis | − | − |
| A-2 | − | − | − | − | − | − | − | NA | − | − | − | − |
| A-3 | − | − | − | − | − | − | − | NA | + | Mild enteritis | − | − |
| A-4 | − | − | − | − | − | − | − | NA | − | − | − | − |
| A-5 | − | − | − | − | − | − | − | NA | + | − | − | − |
| A-6 | − | − | − | − | − | − | − | NA | − | − | − | − |
| A-7 | − | − | − | − | − | − | − | NA | + | Severe enteritis | − | − |
| A-8 | − | − | − | − | − | − | − | NA | + | Moderate enteritis | − | − |
| A-9 | − | − | − | − | − | − | − | NA | − | − | − | − |
| A-10 | − | − | − | − | − | − | − | NA | − | Mild enteritis | − | − |
| A-11 | − | − | − | − | NA | NA | NA | + | NA | − | − | − |
| A-12 | − | − | − | − | NA | NA | NA | + | NA | − | − | − |
| A-13 | − | − | − | − | NA | NA | NA | + | NA | − | − | − |
| A-14 | − | − | − | − | NA | NA | NA | + | NA | − | − | − |
| A-15 | − | − | − | − | NA | NA | NA | + | NA | − | − | − |
| B-1 | − | − | − | − | − | − | − | NA | + | Minimal enteritis | − | − |
| B-2 | − | − | − | − | − | − | − | NA | + | Minimal enteritis | − | − |
| B-3 | − | − | − | − | − | − | − | NA | + | − | − | − |

-continued

| ID | Fecal PCR D0 | Fecal PCR d7 | Fecal PCR d14 | Fecal PCR d21 | Fecal PCR d29 | Fecal PCR d36 | Fecal PCR d43 | Mucosa PCR Day 21 | Mucosa PCR Day 43 | Microscopic Lesions HE stain | Silver | FA |
|---|---|---|---|---|---|---|---|---|---|---|---|---|
| B-4 | − | − | − | − | − | − | − | NA | + | Minimal enteritis | − | − |
| B-5 | − | − | − | − | − | − | − | NA | + | Minimal enteritis | − | − |
| B-6 | − | − | − | − | − | − | − | NA | + | Minimal enteritis | − | − |
| B-7 | − | − | − | − | − | − | − | NA | + | − | − | − |
| B-8 | − | − | − | − | − | − | − | NA | + | − | − | − |
| B-9 | − | − | − | − | − | − | − | NA | + | − | − | − |
| B-10 | − | − | − | − | − | − | − | NA | + | − | − | − |
| B-11 | − | − | − | − | NA | NA | NA | − | NA | − | − | − |
| B-12 | − | − | − | − | NA | NA | NA | − | NA | − | − | − |
| B-13 | − | − | − | − | NA | NA | NA | − | NA | − | − | − |
| B-14 | − | − | − | − | NA | NA | NA | − | NA | − | − | − |
| B-15 | − | − | − | − | NA | NA | NA | − | NA | − | − | − |
| C-1 | − | − | − | − | − | − | − | NA | − | − | − | − |
| C-2 | − | − | − | − | − | − | − | NA | − | − | − | − |
| C-3 | − | − | − | − | − | − | − | NA | − | − | − | − |
| C-4 | − | − | − | − | − | − | − | NA | − | − | − | − |
| C-5 | − | − | − | − | − | − | − | NA | − | − | − | − |
| C-6 | − | − | − | − | − | − | − | NA | − | − | − | − |
| C-7 | − | − | − | − | − | − | − | NA | − | − | − | − |
| C-8 | − | − | − | − | − | − | − | NA | − | − | − | − |
| C-9 | − | − | − | − | − | − | − | NA | − | − | − | − |
| C-10 | − | − | − | − | − | − | − | NA | − | − | − | − |

EXAMPLE 6
Swine Vaccine Efficacy Experiment

Purpose:

The object of this study was to evaluate the safety, persistent colonization and efficacy of an avirulent-live isolate and a killed isolate of L. intracellularis in pigs 2–3 weeks of age. A host animal study was conducted in which pigs 3 weeks of age were vaccinated then exposed to a virulent challenge with L. intracellularis strain N343 to compare differences in protection between the vaccines.

Methods:

On Dec. 11, 1995, a total of 45 pigs, 3 weeks of age were purchased from H & K Farms. They were transported to Veterinary Resources, Inc., a research facility located near Cambridge, Iowa, where they were tagged to individually identify each pig. The pigs were held at this facility for two days prior to initiation of the study to allow acclimation to the facility and were fed antibiotic-free feed throughout the study.

On December 13, all pigs were weighed, bled to collect serum, clinically scored, and rectal swabs collected. The pigs were then randomly divided into groups of five and placed into tubs. Twenty pigs were placed into a separate room and were designated control and strict control groups. Fifteen pigs were placed in a second room for the ISi-1 vaccine. A third room had 10 pigs for ISi-2.

The live vaccine was prepared at the NOBL Laboratories Research and Development facility and identified as experimental serial ISi-1. ISi-1 (strain N343) was isolated from a pig and grown continuously in pure culture for 29 weeks. The vaccine was grown in McCoys cells in spinner flasks at reduced oxygen until approximately 100% infection was observed. A sample of the high passage N343 strain used for ISi-1 was passed an additional 11 weeks ("N343NP40wk") and deposited under the Budapest Treaty on May 22, 1996 in the ATCC, 12301 Parklawn Drive, Rockville, Md. U.S.A. 20852 and assigned Accession Number 55783. The cultures were harvested by centrifuging at 3000×g for 20 minutes. The pellets were resuspended in Sucrose-Phosphate-Glutamate solution (SPG) with 10% FBS and passed 4 times through a 25 gauge needle. The lysates were centrifuged at 500×g for 5 minutes to pellet the debris and microcarrier beads. The supernatant was saved and stored at −70° C. until approximately one hour before vaccination where it was stored on ice until administration.

The killed vaccine (ISi-2) was grown, passed for 12½ weeks and harvested in a similar manner as above and was purified by a percol gradient. The purified bacteria were then stored at −70° C. until approximately 1 week before vaccination in which it was stored at 4° C. at normal atmospheric oxygen levels which becomes toxic to L. intracellularis. AlOH was added to the bacteria to a final mixture of 10% AlOH. Protein concentration was determined using the Biurett method.

Quantitation of Live IS Intracellularis:

Quantitation of viable L. intracellularis was accomplished by determination of the Tissue Culture Infectious Dose 50 percent ($TCID_{50}$). Ninety-six well microtiter plates were seeded with McCoys cells at 1250 cells/well and grown 18–24 hours prior to infection. The samples were serially diluted 1:10 DMEM/5% FBS containing Vancomycin (100 μg/ml) and Amphotericin B (2.0 μg/ml). The dilutions were added to the 96 well microtiter plates with 0.1 ml/well. Twelve wells/dilution were used. The plate was incubated for 6 days at 37° C. and gas concentrations of 8.0% $O_2$, 8.8% $CO_2$ and 83.2% $N_2$. The cells were fixed with cold 50% acetone and 50% methanol for 2 minutes. To the wells, 0.03 ml/well of anti-L. intracellularis monoclonal antibody (developed by Dr. Steven McOrist) diluted 1:2000 in PBS was added. The plate was incubated for 30 minutes at 37° C. and then washed 3 times with PBS. Anti-mouse immunoglobulin G-fluorochrome conjugate (FITC) diluted 1:30 was added at 0.03 ml/well and incubated 30 minutes at 37° C. The plate was washed 3 times with $ddH_2O$ and allowed to dry. Samples were observed on a fluorescent microscope and the TCID$_{50}$/ml was determined using the Reed-Meunsch method of calculation.

TCID$_{50}$ results indicated that ISi-1 had 1.8×10$^5$ bacteria/ml. A fourth inoculum was a placebo and was derived from tissue culture cells processed in the same manner as the vaccines.

The killed vaccine was tested for total protein content using the Biurret method and contained 0.311 mg/ml.

The pigs were vaccinated on Dec. 13, 1995. The live vaccine was all given at a dose of 2 ml IN with 1 ml/nostril. The ISi-2 (killed) vaccine was given IM with 1.5 ml/pig and again 14 days later. All control animals were given non-infected cells in the same manner as the live vaccines.

Observation and Samples:

Fecal swabs and serums were collected at 7 day intervals throughout the study. The fecal swabs were processed for PCR testing using the primer set, 5'-TATGGCTGTCAAACACTCCG-3' and 5'-TGAAGGTATTGGTATTCTCC-3' for the DNA amplifications. Cycle parameters were 93° C. for 5 minutes, 55° C. for 45 seconds, and 72° C. for 45 seconds for the first cycle. Thirty-three cycles were performed at the previously mentioned temperatures for 45 seconds per temperature. The final cycle was 93° C. for 45 seconds, 55° C. for 45 seconds, and 72° C. for 2 minutes, primers defined by Jones et al.

Challenge:

All animals, except strict controls, were given a challenge culture 26 and 27 days post-vaccination consisting of low passage cultures of *L. intracellularis* strains N343 and N72994 that were grown between 8 and 12 weeks continuously. The cultures were harvested by centrifuging at 3000×g for 20 minutes. The pellets were resuspended in Sucrose-Phosphate-Glutamate solution (SPG) with 10% fetal bovine serum and passed 4 times through a 25 gauge needle. Some harvested cultures were stored at −70° C. until time of challenge while others were grown until the day of challenge and harvested. Challenge inoculums were combined and TCID$_{50}$ of the cultures were determined. The samples were stored on ice until administered.

Challenge culture given on Jan. 8, 1996 consisted of 4×10$^4$ bacteria/ml and challenge culture given on Jan. 9, 1996 had 3×10$^4$ bacteria/ml. The pigs were given 15 ml of challenge on both days via gastric lavage. The animals thus received 6×10$^5$ bacteria/pig and 4.7×10$^5$ bacteria/pig on Jan. 8, 1996 and Jan. 9, 1996 respectively.

Results:

Safety:

Fecal PCR results: Detection of *L. intracellularis* using PCR demonstrated that no pigs were shedding the bacteria at the beginning of the study. At seven days post-vaccination all pigs were negative. Fourteen days post-vaccination 3 pigs in the ISi-1 group were positive. Two animals were positive in the ISi-1 group 21 days post-vaccination and all other pigs negative. At day 26 post-vaccination no animals were shedding the bacteria as detected by PCR. Twenty-six day post-vaccination 5 pigs from groups ISi-1 and controls and 4 pigs from group ISi-2 were necropsied. Samples collected were ileum, colon, mesenteric lymph node, and tonsil as well as lung samples from pigs with lesions suspicious for pneumonia.

PCR testing was performed on the individual ileum and lung samples. Tonsil, colon, and lymph nodes were pooled by treatment group and PCR performed. Results of the PCR testing are below.

| Group | PCR of Ileum 26 days Post-Vaccination | Colon Pooled | Tonsil Pooled | Mesenteric Lymph Node Pooled | Lung Pooled |
|---|---|---|---|---|---|
| ISi-1 | 1 of 5 | + | − | − | 1 of 1 |
| ISi-2 | 0 of 4 | − | − | − | 0 of 1 |
| Controls | 0 of 5 | − | − | − | no test |
| Strict Controls | no test | no test | no test | no test | no test |

Histological sections of the ileums were stained using a monoclonal antibody specific for *L. intracellularis* as the primary antibody and anti-mouse immunoglobulin G-fluorochrome conjugate as the secondary antibody. *L. intracellularis* were observed in 3 of the five pigs from ISi-1. All other pigs were negative by fluorescent antibody staining.

The remaining pigs were necropsied 21 days after challenge and the same samples were collected for evaluation. PCR results are listed below.

| Group | PCR of Ileum 21 days Post-Challenge | Colon Pooled | Tonsil Pooled | Mesenteric Lymph Node Pooled | Lung Pooled |
|---|---|---|---|---|---|
| ISi-1 | 0 of 10 | + | − | − | − |
| ISi-2 | 0 of 6 | − | − | − | − |
| Controls | 4 of 10 | − | − | − | − |
| Strict Controls | 0 of 5 | − | − | − | − |

FA stains of the ileums were performed as stated above with 7 of 10 animals positive in the control group. All other animals were negative for the presence of *L. intracellularis*.

The serum was tested for IgG antibody production by the pigs after exposure to *L. intracellularis*. The test was set up by seeding tissue culture treated Terasaki plates with McCoys cells at 125 cells/well and grown 18–24 hours prior to infection. A pure culture of *L. intracellularis* diluted to 1000–3000 bacteria/ml in DMEM with 5% fetal bovine serum was then added to the wells with 0.01 ml/well. The plate was incubated for 6 days at gas concentrations of 8.0% $O_2$, 8.8% $CO_2$ and 83.2% $N_2$ The cells were fixed with cold 50% acetone and 50% methanol for 2 minutes. The serums from the pigs were diluted 1:75 in sterile PBS. The diluted serum was added to the wells at 0.01 ml/well. The plates were then incubated for 30–60 minutes at 37° C. The plates were washed 5 times with sterile PBS. To the wells, 0.01 ml/well of anti-swine IgG immunoglobulin G-fluorochrome conjugate was added. The plate was incubated for 30 minutes at 37° C. The plates were washed 5 times with ddH$_2$O and allowed to dry. Samples washed 5 times with ddH$_2$O and allowed to dry. Samples were observed on a fluorescent microscope and the wells in which bacteria were observed were labeled positive, and wells in which no bacteria were observed were labeled negative.

Results:

| Group | Day 0 | 26 days Post-Vaccination | 47 days Post-Vaccination 21 days Post-Challenge |
|---|---|---|---|
| ISi-1 | 0 of 15 | 6 of 15 | 8 of 10 |
| ISi-2 | 0 of 10 | 3 of 10 | 5 of 6 |

-continued

| Group | Day 0 | 26 days Post-Vaccination | 47 days Post-Vaccination 21 days Post-Challenge |
|---|---|---|---|
| Controls | 1 of 15 | 0 of 15 | 9 of 10 |
| Strict Controls | 0 of 5 | 0 of 5 | 0 of 5 |

Animals that were positive at day 0 were again tested at weekly intervals. Results demonstrated that all became serologically negative by 14 days post-vaccination. This is not unexpected since the age of the pigs at day 0 was three weeks and positive results at that age could be due to maternal antibodies.

The serums were tested along with a positive control serum obtained by hyperimmunizing a pig with *L. intracellularis* grown in pure culture. Negative control serum used was collected from a gnotobiotic pig at South Dakota State University.

The above description and examples are only illustrative of preferred embodiments which achieve the objects, features, and advantages of the present invention, and it is not intended that the present invention be limited thereto. Any modifications of the present invention which come within the spirit and scope of the following claims is considered part of the present invention.

We claim:

1. An avirulent strain of *Lawsonia intracellularis*, wherein said avirulent strain is *Lawsonia intracellularis* deposit strain ATCC No. 55783 or a *Lawsonia intracellularis* strain having all of the identifying characteristics of deposit strain ATCC No. 55783.

2. A vaccine for the immunization of an animal, comprising a pharmaceutically effective amount of an avirulent strain of *Lawsonia intracellurlaris*, wherein said avirulent strain is *Lawsonia intracellurlaris* deposit strain ATCC No. 55783 or a *Lawsonia intracellurlaris* strain having all of the identifying characteristics of deposit strain ATCC No. 55783, and a pharmaceutically acceptable carrier.

3. A method for stimulating the immune system of an animal to respond to an immunogenic antigen of pathogenic Lawsonia, comprising administering to said animal an immunogenic composition containing an avirulent strain of *Lawsonia intracellurlaris*, wherein said avirulent strain is *Lawsonia intracellurlaris* deposit strain ATCC No. 55783 or a *Lawsonia intracellurlaris* strain having all of the identifying characteristics of deposit strain ATCC No. 55783.

4. A method for making an attenuated *Lawsonia intracellularis* strain, comprising the steps of incubating Lawsonia in culture cell which are in suspension at an oxygen concentration of less than about 18 percent.

5. The method of claim 4 comprising the further step of passaging a portion of said cells to fresh cells to increase the production of *L. intracellularis* bacteria.

6. The method of claim 4 wherein said *L. intracellularis* bacteria is obtained from an animal infected with *L. intracellularis*.

7. The method of claim 4 wherein said incubation occurs at an oxygen concentration in the range of from about 0 percent to about 8 percent.

8. The method of claim 4 wherein said incubation occurs at an oxygen concentration in the range of from about 0 percent to about 3 percent.

9. The method of claim 4 wherein said culture cells are selected from the group consisting of HEp-2, McCoy, and IEC-18 cells.

10. The method of claim 9 wherein said McCoy and IEC-18 cells are incubated on microcarriers.

11. A method for making a vaccine for inducing an immune response to *L. intracellularis* bacteria in an animal, comprising the steps of incubating Lawsonia bacteria in culture cells which are in suspension at an oxygen concentration of less than about 18 percent to cultivate said bacteria, and mixing said cultivated bacteria with a pharmaceutically acceptable carrier.

12. The method of claim 11 wherein said Lawsonia bacteria is prepared from an intestinal homogenate of an animal infected with *L. intracellularis*.

13. The method of claim 12 wherein said Lawsonia bacteria is selected from the group consisting of *Lawsonia intracellurlaris* deposit strain ATCC No. 55783, a *Lawsonia intracellularis* strain having all of the identifying characteristics of deposit strain ATCC No. 55783, *Lawsonia intracellularis* deposit strain ATCC No. 55672, and a *Lawsonia intracellularis* strain having all of the identifying characteristics of deposit strain ATCC No. 55672.

14. The method of claim 11 further comprising the step of killing said cultivated bacteria to prepare a vaccine containing killed *L. intracellularis* bacteria.

15. The method of claim 11 further comprising the step of cultivating said bacteria for a sufficient time to produce an attenuated strain.

16. A biologically pure culture of a mammalian host cell infected by an intracellular bacteria, wherein said bacteria is *Lawsonia intracellurlaris* deposit strain ATCC No. 55672 or a *Lawsonia intracellurlaris* strain having all of the identifying characteristics of deposit strain ATCC No. 55672.

17. A vaccine for inducing an immune response to *L. intracellularis* bacteria in an animal, comprising killed *L. intracellularis* bacteria selected from the group consisting of *L. intracellularis* deposit strain ATCC No. 55672, an *L. intracellularis* strain having all of the identifying characteristics of *L. intracellularis* deposit strain ATCC No. 55672, *L. intracellularis* deposit strain ATCC No. 55783, and an *L. intracellularis* strain having all of the identifying characteristics of *L. intracellularis* deposit strain ATCC No. 55783, and a pharmaceutically acceptable carrier.

* * * * *